United States Patent
Birnbaum et al.

(10) Patent No.: US 9,375,558 B2
(45) Date of Patent: *Jun. 28, 2016

(54) METHOD OF TREATING INFECTIONS, DISEASES OR DISORDERS OF NAIL UNIT

(71) Applicant: Hallux, Inc., Laguna Hills, CA (US)

(72) Inventors: Jay E. Birnbaum, Montville, NJ (US); Bruce Lerman, San Jose, CA (US)

(73) Assignee: Hallux, Inc., Laguna Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/707,913

(22) Filed: May 8, 2015

(65) Prior Publication Data

US 2015/0238744 A1    Aug. 27, 2015

Related U.S. Application Data

(63) Continuation of application No. 14/201,320, filed on Mar. 7, 2014.

(60) Provisional application No. 61/784,065, filed on Mar. 14, 2013, provisional application No. 61/877,229, filed on Sep. 12, 2013.

(51) Int. Cl.
| | | |
|---|---|---|
| *A61K 9/00* | (2006.01) | |
| *A61M 37/00* | (2006.01) | |
| *A61K 31/137* | (2006.01) | |
| *A61K 47/10* | (2006.01) | |

(Continued)

(52) U.S. Cl.
CPC .......... *A61M 37/0069* (2013.01); *A61K 9/0024* (2013.01); *A61K 31/07* (2013.01); *A61K 31/135* (2013.01); *A61K 31/137* (2013.01); *A61K 47/10* (2013.01)

(58) Field of Classification Search
CPC ...... A61K 9/0024; A61K 9/16; A61K 9/0012
See application file for complete search history.

(56) References Cited

U.S. PATENT DOCUMENTS

| | | | |
|---|---|---|---|
| 4,144,346 A | 3/1979 | Heeres et al. | |
| 4,180,058 A | 12/1979 | Brem | |

(Continued)

FOREIGN PATENT DOCUMENTS

| | | | |
|---|---|---|---|
| AU | 742061 B2 | 6/1998 | |
| CA | 2326057 A1 | 5/2001 | |

(Continued)

OTHER PUBLICATIONS

International Search Report from PCT Patent Application No. PCT/US2003/008030 mailed Mar. 13, 2003, application now published as International Publication No. WO 2003/082188 published Oct. 9, 2003.

(Continued)

*Primary Examiner* — Leslie Deak
*Assistant Examiner* — Kai Weng
(74) *Attorney, Agent, or Firm* — Judy M. Mohr; McDermott Will & Emery LLP

(57) ABSTRACT

Methods for the subungual treatment of diseases or disorders of the nail unit including infections, especially fungal infections, and nail psoriasis involving the toenails and fingernails are described. The methods provide a technique for placement of a drug-containing composition subungually with reduced risk of hematoma formation and improved patient comfort.

20 Claims, 6 Drawing Sheets

(51) Int. Cl.
*A61K 31/07* (2006.01)
*A61K 31/135* (2006.01)

(56) References Cited

U.S. PATENT DOCUMENTS

| | | |
|---|---|---|
| 4,223,036 A | 9/1980 | Heeres et al. |
| 4,250,164 A | 2/1981 | Bernstein |
| 4,263,289 A | 4/1981 | Edwards |
| 4,267,179 A | 5/1981 | Heeres et al. |
| 4,404,216 A | 9/1983 | Richardson |
| 4,490,395 A | 12/1984 | Cherukuri et al. |
| 4,568,536 A | 2/1986 | Kronenthal et al. |
| 4,569,837 A | 2/1986 | Suzuki et al. |
| 4,636,520 A | 1/1987 | Umio et al. |
| 4,685,883 A | 8/1987 | Jernberg |
| 4,780,320 A | 10/1988 | Baker |
| 4,892,736 A | 1/1990 | Goodson |
| 4,919,939 A | 4/1990 | Baker |
| 4,957,730 A | 9/1990 | Bohn et al. |
| 5,002,769 A | 3/1991 | Friedman |
| 5,002,938 A | 3/1991 | Wang et al. |
| 5,023,082 A | 6/1991 | Friedman et al. |
| 5,059,123 A | 10/1991 | Jernberg |
| 5,063,049 A | 11/1991 | Billings |
| 5,110,809 A | 5/1992 | Wang et al. |
| 5,120,530 A | 6/1992 | Ferro et al. |
| 5,197,882 A | 3/1993 | Jernberg |
| 5,219,877 A | 6/1993 | Shah et al. |
| 5,264,206 A | 11/1993 | Bohn et al. |
| 5,324,520 A | 6/1994 | Dunn et al. |
| 5,346,692 A | 9/1994 | Wohlrab et al. |
| 5,391,367 A | 2/1995 | DeVincentis et al. |
| 5,422,370 A | 6/1995 | Yu et al. |
| 5,464,610 A | 11/1995 | Hayes, Jr. et al. |
| 5,487,776 A | 1/1996 | Nimni |
| 5,547,988 A | 8/1996 | Yu et al. |
| 5,587,152 A | 12/1996 | Mackles et al. |
| 5,597,849 A | 1/1997 | McGinity et al. |
| 5,630,796 A | 5/1997 | Bellhouse et al. |
| 5,696,105 A | 12/1997 | Hackler |
| 5,705,181 A | 1/1998 | Cooper et al. |
| 5,814,305 A | 9/1998 | Laugier et al. |
| 5,855,904 A | 1/1999 | Chung et al. |
| 5,869,079 A | 2/1999 | Wong et al. |
| 5,894,020 A | 4/1999 | Concha |
| 5,916,545 A | 6/1999 | Burnett et al. |
| 5,947,956 A | 9/1999 | Karell |
| 5,993,790 A | 11/1999 | Strauss |
| 6,008,173 A | 12/1999 | Chopra et al. |
| 6,043,063 A | 3/2000 | Kurdikar et al. |
| 6,120,789 A | 9/2000 | Dunn |
| 6,123,957 A | 9/2000 | Jernberg |
| 6,143,794 A | 11/2000 | Chaudhuri et al. |
| 6,162,420 A | 12/2000 | Bohn et al. |
| 6,207,142 B1 | 3/2001 | Odds et al. |
| 6,221,903 B1 | 4/2001 | Chourchesne |
| 6,224,887 B1 | 5/2001 | Samour et al. |
| 6,231,840 B1 | 5/2001 | Buck |
| 6,264,927 B1 | 7/2001 | Monahan |
| 6,270,472 B1 | 8/2001 | Antaki et al. |
| 6,361,785 B1 | 3/2002 | Nair et al. |
| 6,386,869 B1 | 5/2002 | Zegarelli |
| 6,391,879 B1 | 5/2002 | Reeves |
| 6,495,124 B1 | 12/2002 | Samour |
| 6,517,863 B1 | 2/2003 | LaTorre et al. |
| 6,676,953 B2 | 1/2004 | Hexamer |
| 6,727,401 B1 | 4/2004 | Venkateshwaran et al. |
| 6,733,751 B2 | 5/2004 | Farmer |
| 6,846,837 B2 | 1/2005 | Maibach et al. |
| 6,878,365 B2 | 4/2005 | Brehove |
| 7,074,392 B1 | 7/2006 | Friedman et al. |
| 7,074,426 B2 | 7/2006 | Kochinke |
| 7,135,194 B2 | 11/2006 | Birnbaum |
| 7,138,179 B2 | 11/2006 | Kim et al. |
| 8,354,095 B2 | 1/2013 | Kochinke et al. |
| 8,591,870 B2 | 11/2013 | Kochinke et al. |
| 8,747,820 B2 | 6/2014 | Kochinke et al. |
| 2001/0008961 A1 | 7/2001 | Hecker et al. |
| 2002/164374 A1 | 11/2002 | Jackson et al. |
| 2002/0173436 A1 | 11/2002 | Sonnenberg et al. |
| 2002/0183387 A1 | 12/2002 | Bogart |
| 2003/0007939 A1 | 1/2003 | Murad |
| 2003/0049307 A1 | 3/2003 | Gyurik |
| 2003/0072807 A1 | 4/2003 | Wong et al. |
| 2003/0118649 A1 | 6/2003 | Gao et al. |
| 2003/0130225 A1 | 7/2003 | Ahmad et al. |
| 2003/0185872 A1 | 10/2003 | Kochinke et al. |
| 2003/0207971 A1 | 11/2003 | Stuart, Jr. et al. |
| 2003/0235541 A1 | 12/2003 | Maibach et al. |
| 2004/0062733 A1 | 4/2004 | Birnbaum |
| 2004/0137059 A1 | 7/2004 | Nivaggioli et al. |
| 2004/0197280 A1 | 10/2004 | Repka |
| 2005/0042293 A1 | 2/2005 | Jackson et al. |
| 2005/0065393 A1 | 3/2005 | Miller et al. |
| 2006/0067898 A1 | 3/2006 | Kepka et al. |
| 2006/0106363 A1 | 5/2006 | Aravana et al. |
| 2006/0112503 A1 | 6/2006 | Hatano et al. |
| 2006/0153786 A1 | 7/2006 | Kochinke et al. |
| 2006/0204548 A1 | 9/2006 | Nivaggioli et al. |
| 2006/0212021 A1 | 9/2006 | Yazaki et al. |
| 2006/0275230 A1 | 12/2006 | Kochinke et al. |
| 2007/0014743 A1 | 1/2007 | Birnbaum |
| 2007/0123797 A1 | 5/2007 | Krause |
| 2007/0275044 A1 | 11/2007 | Potter et al. |
| 2008/0132442 A1 | 6/2008 | Kochinke et al. |
| 2008/0261986 A1 | 10/2008 | Friden et al. |
| 2008/0299165 A1 | 12/2008 | Tao et al. |
| 2008/0317844 A1 | 12/2008 | Dudley et al. |
| 2009/0004272 A1 | 1/2009 | Gibson et al. |
| 2009/0093787 A1 | 4/2009 | Barbour |
| 2009/0105749 A1 | 4/2009 | De Juan et al. |
| 2009/0131908 A1 | 5/2009 | McKay |
| 2009/0247939 A1 | 10/2009 | Rue et al. |
| 2010/0048724 A1 | 2/2010 | Birnbaum et al. |
| 2011/0104235 A1 | 5/2011 | Kochinke et al. |
| 2013/0122097 A1 | 5/2013 | Bright et al. |
| 2014/0050772 A1 | 2/2014 | Kochinke et al. |
| 2014/0276477 A1 | 9/2014 | Birnbaum et al. |
| 2014/0322293 A1 | 10/2014 | Kochinke et al. |

FOREIGN PATENT DOCUMENTS

| | | |
|---|---|---|
| DE | 19836436 A1 | 3/1999 |
| EP | 0024587 A1 | 3/1981 |
| EP | 0952171 A2 | 10/1999 |
| EP | 1477187 A1 | 11/2004 |
| GR | 30306696 | 12/2001 |
| JP | 8231430 A | 9/1996 |
| KR | 20010044625 | 6/2001 |
| KR | 20010046941 | 6/2001 |
| RU | 2062607 C1 | 6/1996 |
| RU | 2083224 C1 | 7/1997 |
| RU | 2127118 C1 | 3/1999 |
| RU | 2134568 C1 | 8/1999 |
| RU | 2146139 C1 | 3/2000 |
| RU | 2159148 C2 | 11/2000 |
| RU | 2161502 C2 | 1/2001 |
| RU | 2164418 C2 | 3/2001 |
| RU | 2165265 C2 | 4/2001 |
| RU | 2176525 C2 | 12/2001 |
| RU | 2196555 C2 | 1/2003 |
| RU | 2197964 C2 | 2/2003 |
| RU | 2207845 C2 | 7/2003 |
| RU | 2001129096 C2 | 9/2003 |
| RU | 2215542 C2 | 11/2003 |
| RU | 2232779 C2 | 7/2004 |
| RU | 2234337 C2 | 8/2004 |
| SU | 1122323 A | 11/1984 |
| WO | WO 89/08449 A1 | 9/1989 |
| WO | WO 91/04058 A2 | 4/1991 |
| WO | WO 92/00718 A1 | 1/1992 |
| WO | WO 95/03775 A1 | 2/1995 |
| WO | WO 95/09590 A1 | 4/1995 |
| WO | WO 95/31178 A1 | 11/1995 |

(56) References Cited

FOREIGN PATENT DOCUMENTS

| | | |
|---|---|---|
| WO | WO 96/16643 A1 | 6/1996 |
| WO | WO 96/32107 A1 | 10/1996 |
| WO | WO 96/32419 A1 | 10/1996 |
| WO | WO 96/36317 A1 | 11/1996 |
| WO | WO 96/40072 A2 | 12/1996 |
| WO | WO 97/15282 A1 | 5/1997 |
| WO | WO 98/52927 A1 | 11/1998 |
| WO | WO 99/15210 A2 | 4/1999 |
| WO | WO 99/21908 A1 | 5/1999 |
| WO | WO 99/42147 A1 | 8/1999 |
| WO | WO 00/18821 A1 | 4/2000 |
| WO | WO 01/45742 A1 | 6/2001 |
| WO | WO 02/092661 A1 | 11/2002 |
| WO | WO 03/082188 A2 | 10/2003 |
| WO | WO 2004/000291 A1 | 12/2003 |
| WO | WO 2004/002456 A1 | 1/2004 |
| WO | WO 2004/060396 A2 | 7/2004 |
| WO | WO 2004/084826 A2 | 10/2004 |
| WO | WO 2006/063350 A2 | 6/2006 |
| WO | WO 2006/086888 A1 | 8/2006 |
| WO | WO 2007/139804 A2 | 12/2007 |
| WO | WO 2011/063349 A1 | 5/2011 |
| WO | WO 2011/087867 A1 | 7/2011 |
| WO | WO 2014/159060 A1 | 10/2014 |

OTHER PUBLICATIONS

International Search Report from PCT Patent Application No. PCT/US2010/057663 mailed Jan. 12, 2011, application now published as International Publication No. WO 2011/063349 published May 26, 2011.

Nesci et al., "Control of aspergillus growth and aflatoxin production using antioxidants at different conditions of water activity and pH", J. Applied Microbio., vol. 95, pp. 279-287 (2003).

Netters Essential Histology, $2^{nd}$ Edition, Ovalle and Nahirney, Ed., Elsevier Health Sciences, pp. 261 (2013).

Barclay, "Pulsed terbinafine helpful for onychomycosis", Medscape Medical News, 1 page, Jun. 23, 2004.

"Between", Chambers $21^{st}$ Century Dictionary, London, Chambers Harrap Publishers Limited (2001), accessed online at http://www.credoreference.com/entry/chambdict/between, 2 pages, Oct. 28, 2013.

Encyclopedic Dictionary of Medical Terms, "Meditsina," pp. 326 and 807, 5 pgs. (2001) English translation included.

Favre et al., "Comparison of in Vitro Activities of 17 Antifungal Drugs a Panel of 20 Dermatophytes by Using a Microdilution Assay," Journal of Clinical Microbiology, vol. 41, No. 10, pp. 4817-4819 (2003).

International Search Report from PCT Patent Application No. PCT/US2005/044930 mailed Jun. 15, 2006, application now published as International Publication No. WO 2006/063350 published Jun. 15, 2006.

International Search Report from PCT Patent Application No. PCT/US2007/012243 mailed Nov. 30, 2007, application now published as International Publication No. WO 2007/139804 published Dec. 6, 2007.

International Search Report from PCT Patent Application No. PCT/US2010/061922 mailed Feb. 24, 2011, application now published as International Publication No. WO 2011/087867 published Jul. 21, 2011.

International Search Report from PCT Patent Application No. PCT/US2014/021786 mailed Jun. 12, 2014, application now published as International Publication No. WO 2014/159060 published Oct. 2, 2014.

Karaca et al., "In Vitro Susceptibility Testing of Dermatophytes: Comparison of Disk Diffusion and Reference Broth Dilution Methods," Diagnostic Microbiology and Infectious Disease, vol. 48, pp. 259-264 (2004).

Lechenko, "Fungal Infections of the Skin. Contemporary Antimycoticks Before Dermatology," Comsilium Medicum, vol. 6, No. 3, 17 pgs. (2004) English machine translation included Located Online at <http:/www.medarena.ru/preparats/g-richter/includes/terbisil-st2.asp>.

Mashkovsky, "Drug Guide," vol. II, Moscow, Co. Ltd, pp. 156, 352-353, 356, 358-359, 362, 377-378, 25 pgs. (2001) English machine translation included.

Minghetti et al., "Dermal Patches for the Controlled Release of Miconazole: Influence of the Drug Concentration on the Technological Characteristics," Drug Development and Industrial Pharmacy, vol. 25, No. 5, pp. 679-684 (1999).

METHOD OF TREATING INFECTIONS, DISEASES OR DISORDERS OF NAIL UNIT

CROSS-REFERENCE TO RELATED APPLICATIONS

This application is a continuation of U.S. application Ser. No. 14/201,320, filed Mar. 7, 2014, which claims the benefit of U.S. Provisional Application No. 61/784,065, filed Mar. 14, 2013 and of U.S. Provisional Application No. 61/877,229, filed Sep. 12, 2013, each incorporated is herein by reference in its entirety.

TECHNICAL FIELD

The subject matter described herein relates to compositions and to methods for the subungual (under the nail) treatment of diseases or disorders including infections, especially fungal infections, of the toenails and fingernails (onychomycosis) and nail psoriasis.

BACKGROUND

Nail infections are common conditions of the nail. Onychomycosis, a fungal infection of the nail bed, matrix, or nail plate, is the most common nail infection. The primary clinical features of onychomycosis are distal onycholysis (separation of the nail plate from the nail bed), subungual hyperkeratosis, and a dystrophic, discolored nail. Patients afflicted with onychomycosis are usually embarrassed by their nail disfigurement, but the infection is more than a cosmetic problem. It can sometimes limit mobility and indirectly decrease peripheral circulation, thereby worsening conditions such as venous stasis and diabetic ulcers. Fungal infections of the nail can also spread to other areas of the body and potentially to other persons. The fungal infection can be caused by dermatophytes (e.g., *Trichophyton rubrum* and *T. mentagrophytes*), but may also be due to infection by *Candida* species or non-dermatophyte molds such as *Aspergillus* species, *Scopulariosis brevicaulis*, *Fusarium* species, and *Scytalidium* species.

Currently, oral antifungal agents are the mainstay of treatment for onychomycosis. For example, Sporonox®. capsules (itraconazole) (Janssen Pharmaceutica Products, L.P., Titusville, N.J. and Ortho Biotech Products, L.P., Raritan, N.J.), Lamisil® tablets (terbinafine hydrochloride) (Novartis Pharmaceuticals, East Hanover, N.J.), Diflucan tablets and fluconazole (Pfizer, New York, N.Y.) are commonly prescribed antifungal agents. However, these oral antifungal products are associated with many minor systemic side effects such as headaches, stomach upset, skin rashes, and photosensitivity, as well as serious systemic side effects such as heart failure and liver failure. Although oral antifungal therapy is preferred, risk of the serious side effects often outweighs therapeutic benefit, and drug-drug interactions are a problem for many patients. The prolonged treatment regimen of one dose daily for at least three months, or once weekly for nine to twelve months also leads to poor patient compliance with oral antifungal therapy.

Topical therapy with antifungal agents is an alternative to oral therapy, and a topical solution, Penlac® nail lacquer (ciclopirox solution, 8%) (Dermik Laboratories, Berwyn, Pa.), is approved by the FDA for the topical treatment of mild to moderate onychomycosis. However, the topical mode of administration is seldom effective to treat more than mild nail unit infections because the active agent is unable to effectively penetrate the nail. Topical therapy accompanied by chemical or physical abrasion of the nails has also been largely unsuccessful. Topical antifungal therapy usually also involves daily application to the nails for several months, and thus, also poses a compliance problem. Topical nail treatment typically precludes the use of nail cosmetics/polish that otherwise would be used to camouflage the diseased and/or disfigured nail plate.

Psoriasis is estimated to affect approximately 2% of the population. As many as 50% of psoriasis patients may have nail involvement (psoriatic nail disease or nail psoriasis) with a lifetime incidence in psoriasis patients reaching 80-90%. Nail disease without cutaneous involvement is present in an estimated 5-10% of psoriasis patients. Common features of nail psoriasis include pitting (present in an estimated 68% of affected patients), onycholysis (in 67%), subungual hyperkeratosis (in 25%), oil drop signs (discoloration), crumbling of the nail plate, and splinter hemorrhage, the latter four of these being associated with nail bed involvement. In addition to the obvious cosmetic problem, many patients with nail psoriasis, especially when the fingernails are involved, suffer pain, loss of manual dexterity, and diminished sensation of touch. Onychomycosis may additionally be present with nail psoriasis.

Medications that have been used with varying degrees of success in treating nail psoriasis include corticosteroids (e.g. betamethasone dipropionate, clobetasol, triamcinolone acetonide), vitamin D analogs or derivatives (e.g. calcipitriol, calcipotriene, tacalcitol, calcitriol), retinoids (tazarotene, etretinate), biologicals (e.g. infliximab, adalimumab), antimetabolite drugs such as 5-fluorouracil, and immunosuppressants/calcineurin inhibitors such as cyclosporine and tacrolimus. Topical application of medications has limited use as the medication may not penetrate the nail plate to reach the affected area. Specifically for psoriasis involving the nail bed, where onycholysis and subungual hyperkeratosis are prominent, topically applied antipsoriatic agents have limited transungual penetration into the affected nail bed. Corticosteroid injections into the nail bed have been used with varying results.

Overall, treatment of diseases of the nail unit remains challenging and there remains a continuing need for the development of effective means for the treatment of diseases of the nail unit, particularly diseases that call for delivery of active ingredient to the nail unit for sustained periods of time. An additional need is for treatments that minimize pain.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a method for treating a disease or disorder of the nail unit is provided. In one embodiment, the disorder of the nail unit is an infection such as a fungal infection, such as onychomycosis. The method comprises providing a device comprised of an applicator and a composition comprising an active agent such as an antifungal agent or an anti-psoriatic agent; inserting the applicator subungually; and depositing the composition subungually.

In one embodiment, the applicator comprises a needle and the composition is disposed in the needle tip. In embodiments, the needle has a bevel tip and the composition is disposed at least partially in the bevel tip.

In another embodiment, the applicator comprises a cannula, which may have a blunt distal end or tip. In embodiments, the composition is disposed in the cannula, which will have at least one opening for depositing the composition. In another embodiment, the applicator comprises a cannula and a needle that is sized to have the same or higher (finer) gauge than the cannula. In other embodiments, the composition is deposited subungually from the needle, while the cannula remains at least partially inserted subungually. In other embodiments, the composition is deposited from the needle portion of the needle-cannula applicator after the cannula is withdrawn from its subungual position. In other embodiments, the composition is deposited from the needle portion of the needle-cannula applicator simultaneously with withdrawal of the cannula from its subungual position.

In another embodiment, the method further comprises, prior to inserting the applicator, placing the needle or cannula on the exterior surface of the nail and placing a depth marker on the needle or cannula to mark the desired insertion depth. In one embodiment, the needle or cannula is placed on the exterior surface of the nail such that a distal end of the bevel tip or end touches a distal edge of the lunula, and the depth marker is placed on the needle or cannula where it aligns with the hyponychium.

In a further embodiment, the method further comprises, prior to inserting the applicator, placing the needle or cannula on the exterior surface of the nail such that a distal end of the needle or the cannula approximately aligns with or extends just beyond the most proximal point of a fungal infection or other disease indication in the nail or the nail bed, and a depth marker is placed on the needle or cannula where it aligns with the hyponychium.

In still another embodiment, the step of inserting comprises inserting the needle or cannula past the hyponychium and between the nail plate and the nail bed at least until the depth marker is aligned with the hyponychium. In some embodiments, the step of inserting the needle or cannula comprises inserting above the hyponychium and under the nail plate, or through the hyponychium and under the nail plate. In some embodiments, the insertion is done at the point of highest curvature midway between the lateral fold and midline of the nail.

In yet another embodiment, the step of inserting comprises inserting the needle or cannula at a position between the nail fold and a longitudinal midline of the nail plate.

In other embodiments, the method further comprises after inserting and prior to depositing, withdrawing the needle or cannula to a region between the distal edge of the lunula and the hyponychium.

In another embodiment, the steps of providing, inserting and depositing are repeated to place a subsequent composition subungually. The subsequent composition may be the same as or different than a first composition deposited. The subsequent composition may be deposited at a same or different site than the first composition deposited.

In another embodiment, the applicator comprises a cannula having a blunt end and a needle. The inserting step comprises inserting the cannula past the hyponychium and between the nail plate and the nail bed to a desired depth to create a channel or space in the subungual space. Inserting the cannula past the hyponychium can include, in some embodiment, inserting the cannula above the hyponychium or through the hyponychium by piercing the hyponychium. The cannula is typically withdrawn and the needle is then inserted at least partially into the channel formed by the cannula to a desired depth.

In one embodiment, the composition is a solid composition, sometimes referred to herein as an 'implant', or is a semi-solid composition or a composition in the form of a solution or liquid. In embodiments, the composition comprises an antifungal agent or an anti-psoriatic agent.

In one embodiment, the solid or semi-solid composition is comprised of a biodegradable polymer.

In another embodiment, the biodegradable solid composition or implant is comprised of a polymer having a melting temperature (Tm) greater than the temperature of the nail bed.

In another embodiment, the antifungal agent is released by erosion or degradation of the polymer over a period of at least about 2 weeks, alternatively over a period of at least about 4 weeks.

In one embodiment, the antifungal agent is released to provide an initial burst of active agent followed by a period of extended release of active agent. In one embodiment, the period of extended release comprises at least 10 days, preferably 2 weeks, more preferably at least 4 weeks.

In another embodiment, the composition is comprised of polyethylene glycol with a molecular weight of between 1,000-8,000 Daltons. In still another embodiment, the composition is comprised of the antifungal agent distributed within a polyethylene glycol with a molecular weight of between 2,000-5,000 Daltons. In yet another embodiment, the composition comprises less than about 40 weight percent polyethylene glycol. In another embodiment, the composition comprises at least about 60 weight percent active agent. In another embodiment, the composition comprises between about 65-80 weight percent active agent.

In one embodiment, the antifungal agent is terbinafine hydrochloride or is terbinafine free base. In another embodiment, the antifungal agent is naftifine. In an embodiment, the anti-psoriatic agent is selected from the group consisting of steroids, vitamin A or derivatives, vitamin D or derivatives, calcineurin inhibitors and an anti-metabolite.

In other embodiments, the composition comprises a liquid carrier. In one embodiment, the liquid carrier is a silicone oil.

In one embodiment, the liquid composition (solution or suspension) comprises between about 0.5-5 weight percent anti-fungal agent. In a preferred embodiment, the anti-fungal agent is terbinafine hydrochloride or terbinafine free base. In another embodiment, the anti-fungal agent is naftifine.

In another embodiment, the active agent is an anti-psoriatic agent. In embodiments, the anti-psoriatic agent is selected from steroids, vitamin A or derivatives, vitamin D or derivatives, a calcineurin inhibitor, and an anti-metabolite.

In one embodiment, the composition is an immediate release composition for release of the active agent. In embodiments, the composition provides for release of the active agent within 10 minutes to 2 hours after administration.

In a further embodiment, the composition is a delayed release composition for release of the active agent. In some embodiments, the composition provides for release of the active agent for days to weeks after administration. In additional embodiments, the composition provides for release of the active agent for 2-4 weeks after administration.

In an embodiment, the disease or disorder of the nail unit is onychomycosis exhibiting lateral edge nail involvement.

In another aspect, a dosing regimen for treating a disease or disorder of the nail unit is provided. The regimen comprises administering subungually a first device and a second device, the first and second devices each comprised of a biodegradable polymeric matrix and an active agent dispersed in the matrix. Then, a period of time is allowed to pass and a third device and optionally a fourth device is/are administered, the third device and optional fourth device are comprised of a biodegradable polymeric matrix and an active agent dispersed in the matrix. The period of time that passes achieves release of the active agent from the matrix at a rate to maintain a concentration of active agent in a substantial portion of the nail bed above the minimum inhibitory concentration; and the administering comprises depositing the devices at a position between a lateral nail fold and a longitudinal midline of the nail plate. In an embodiment, the disease or disorder of the nail unit is onychomycosis and the active agent is an antifungal agent. In another embodiment, the disease or disorder of the nail unit is nail psoriasis and the active agent is an anti-psoriatic agent. In a further embodiment, the disease or disorder of the nail unit exhibits lateral edge nail involvement.

In one embodiment, the steps of administering comprise placing a needle or cannula on the exterior surface of the nail plate such that a distal end of the needle or cannula touches a distal edge of the lunula, and placing a depth marker on the needle where it aligns with the hyponychium.

In another embodiment, the step of administering comprises placing a needle or cannula on an exterior surface of the nail such that a distal end of the needle or cannula approximately aligns with or extends just beyond a proximal point of a fungal infection in the nail, and placing a depth marker on the needle where it aligns with the hyponychium. In yet another embodiment, the step of administering comprises placing a needle or cannula on an exterior surface of the nail such that a distal end of the needle or cannula approximately aligns with or extends just beyond a proximal point of disease in the nail, and placing a depth marker on the needle where it aligns with the hyponychium.

In one embodiment, the step of administering comprises inserting the needle or cannula past the hyponychium and between the nail plate and the nail bed until the depth marker is aligned with the hyponychium.

In other embodiments, the step of administering comprises withdrawing the needle or cannula to a region between the distal edge of the lunula and the hyponychium.

In yet another embodiment, waiting a period of time comprises waiting at least about two weeks, alternatively in another embodiment, waiting a period of time comprises waiting at least about four weeks.

In a further embodiment, the dosing regimen further comprises inserting a cannula past the hyponychium and between the nail plate and the nail bed to create a channel or space in the subungual space prior to administering the active agent.

In addition to the exemplary aspects and embodiments described above, further aspects and embodiments will become apparent by reference to the drawings and by study of the following descriptions.

Additional embodiments of the present methods, regimens, devices, systems, compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1A:
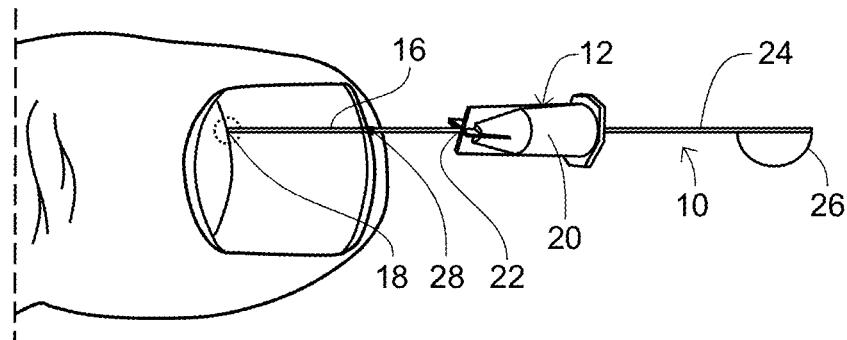
FIGS. 1A-1F illustrate a procedure for inserting an implant subungually in accord with one embodiment.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

II. Method of Treatment

In one aspect, a method for treating infection disease or disorder of the nail unit is provided. The method comprises providing a device comprised of an applicator and a composition comprising a therapeutic or active agent; inserting the applicator subungually; and depositing the composition subungually. Before describing the method and implantation procedure in detail, it is useful to provide information on the nail unit.

The human nail comprises several parts including, but not limited to, the nail matrix, the nail bed, the nail plate, the nail folds, the hyponychium, and the cuticle. The nail plate (fingernail or toenail) is produced by the matrix and progresses toward the tip of the fingers or toes as new plate is formed. The primary function of the nail plate is to protect the underlying digit. The cutaneous tissue framing the nail unit, and which invaginates proximal and lateral to the nail plate, is referred to as the nail folds. The nail matrix is located beneath the proximal nail fold, and is the germinative portion of the nail unit that produces the nail plate. The lunula is the whitish crescent-shaped base of the nail and is the visible part of the nail matrix. The eponychium (or cuticle) is an outgrowth of the proximal fold, situated between the skin of the digit and the proximal end of the nail plate, fusing these structures together. The hyponychium is epithelial tissue located beneath the distal end of the nail plate at the junction between the free edge of the nail plate and the skin of the digit (finger or toe). It forms a seal that protects the nail bed. The nail bed is the layer of tissue underneath the nail between the lunula and the hyponychium.

With reference now to FIGS. 1A-1F, a method of treatment wherein a composition comprising a therapeutic or active agent is administered subungually is illustrated. A device 10 is comprised of an applicator 12 and a composition 14 (seen best in FIGS. 1E-1F). The applicator can take many forms, and the embodiment shown in the drawing is merely exemplary. In this embodiment, applicator 12 is comprised of a needle 16 with a distal tip or end 18. In another embodiment, the applicator 12 is comprised of a cannula with a distal tip or end 18. A cannula for use in the present methods typically has a substantially blunt or rounded end for atraumatic introduction of the cannula under the nail plate. One exemplary cannula is a dermatological cannula such as a micro-cannula used for filler injections. One particular cannula is the micro-cannula available from Inex. A cannula alone may be used for subungual delivery of the therapeutic or active agent. Use of a cannula is particularly useful where the disease or disorder involves onycholysis or where subungual debris has accumulated as it is not necessary to pierce the nail unit for delivery of the therapeutic or active agent. In yet another embodiment, the applicator 12 is comprised of a cannula and a needle. The distal tip of the needle and/or the cannula is dimensioned to contain or hold a composition, particularly when the composition is a solid or semi-solid composition as discussed below. In embodiments where the composition is in the form of a flowable solution (which may after implantation become semi-solid or solid), the needle/cannula and distal tip are dimensioned to permit dispensing of the flowable composition with a force applied by a user. The composition in the embodiment shown in FIGS. 1A-1F is a solid or semi-solid implant, for purposes of illustration, and is contained in the distal tip of the needle or cannula prior to insertion and/or implantation subungually. In some embodiments, the distal tip of the needle is beveled, and the implant (e.g., a solid composition) is situated in the beveled tip. In other embodiments, the implant is situated in the distal tip of the cannula. In one embodiment, the device as provided to the user comprises the composition situated in the distal tip of the needle or cannula. In other embodiments, the composition is provided with the device in a separate packaging unit from the applicator, and the user prior to implantation situates the solid composition into the distal tip of the needle or cannula, or, more generally, situates the solid composition into the applicator.

The applicator may also comprise a handling member, such as the finger-tip hub 20 of applicator 12. A proximal end 22 of needle or cannula 16 extends into the handling member, and in one embodiment is secured within the handling member. The applicator may also comprise a stylet or plunger 24. Stylet 24 is dimensioned to be insertable into the proximal end of needle or cannula 16, and to travel a distance in the bore of needle or cannula 16 sufficient to dispense an implant situated in the needle or cannula. The stylet may optionally include a handle, such as handle 26, at its proximal end to ease handling by a user.

Use of the applicator is described below with reference to the embodiment where the applicator comprises a needle. It will be appreciated that the embodiment where the applicator comprises a cannula is equally contemplated unless otherwise noted. It will further be appreciated that the description of the applicator below applies equally to a cannula and needle in the embodiment where a cannula is subungually inserted prior to insertion of a needle. Use of the applicator is further described below with reference to the embodiment where the disorder or disease of the nail unit is an infection. It will be appreciated that use of the applicator as described is equally applicable to other disorders or diseases of the nail unit unless otherwise noted.

With reference to FIG. 1A, administration of the composition subungually comprises placing the needle on the top of the nail plate such that the distal tip of the needle is approximately aligned above or touches the distal edge of the lunula. When aligning the distal tip with the distal edge of the lunula, the needle is placed on the top (or exterior surface) of the nail plate approximately one-third of the way across the nail unit, as depicted in FIG. 1A. It will be appreciated that the needle may be placed more or less than one-third of the way across the nail unit depending on the subject and desired treatment. Stated alternatively, the needle is placed on the exterior nail plate in a region defined by a longitudinal (intending a line extending from the free margin or distal edge of the nail plate to the eponychium) midline of the nail plate and a lateral nail fold. For convenient reference, the longitudinal line defined by placement of the needle, as just described, is referred to as the "needle placement line." In one embodiment, the needle placement line is in the region defined by the longitudinal midline and a lateral nail fold where the radius of curvature is greatest. In general, the optimal site(s) for individualized insertion should be determined. The needle placement line may then be determined by the optimal insertion site(s). Generally, optimal sites have reduced adherence of the nail plate to the nail bed to allow for easier insertion of the needle and/or cannula. Thus, onycholytic areas tend to be optimal for insertion. In other embodiments, areas exhibiting subungual hyperkeratotic areas, especially after debridement of the area, may be optimal insertion site(s). In other embodiments, the area of the nail plate having the greatest radius of curvature between the nail plate midline and the lateral folds. With the needle in the needle placement line, an indicator mark along the needle shaft where it meets the hyponychium is noted. This may involve noting which of a series of pre-made indicator marks on the needle aligns with the hyponychium or it may involve the user making a mark, such as indicator mark 28 in FIGS. 1A-1E. As will be described, the indicator mark serves as a depth guide for inserting the needle subungually (and depositing the composition into nail bed tissue or into a subungual space). It will be appreciated that the indicator mark 28 may indicate an insertion depth that is less than or greater than the distal edge of the lunula.

Figure 1B:
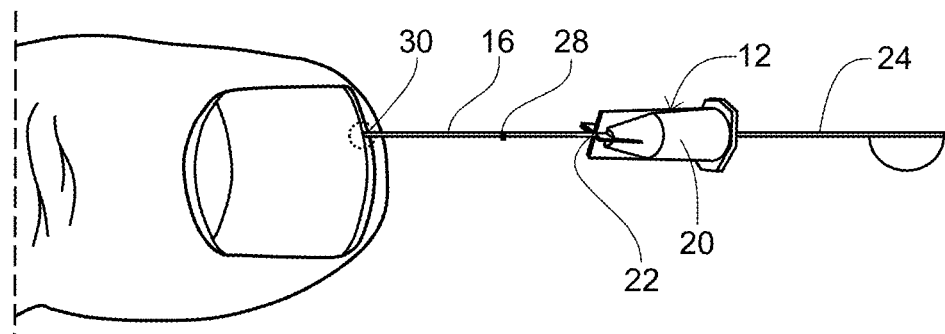
Figure 1C:
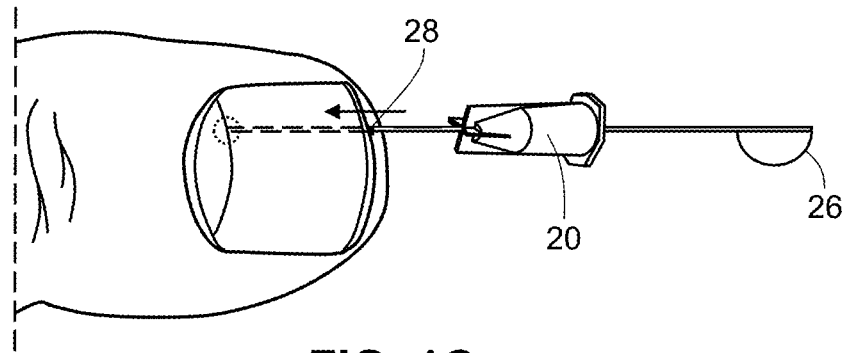

With reference to FIG. 1B, the needle is placed at a desired insertion point, indicated at 30 in FIG. 1B. The insertion point, in one embodiment, is at the level of the hyponychium along the needle placement line. This is illustrated in FIG. 1B, where the distal tip of the needle is positioned at the hyponychium along the needle placement line (see in FIG. 1A). As seen in FIG. 1C, the distal tip of the needle is inserted past the hyponychium, under the nail plate and into the space above the nail bed and under the nail plate. In embodiments, the needle may be inserted at least partially into the nail bed. The needle is inserted until the indicator mark 28 is aligned with the hyponychium (FIG. 1C).

Figure 1D:
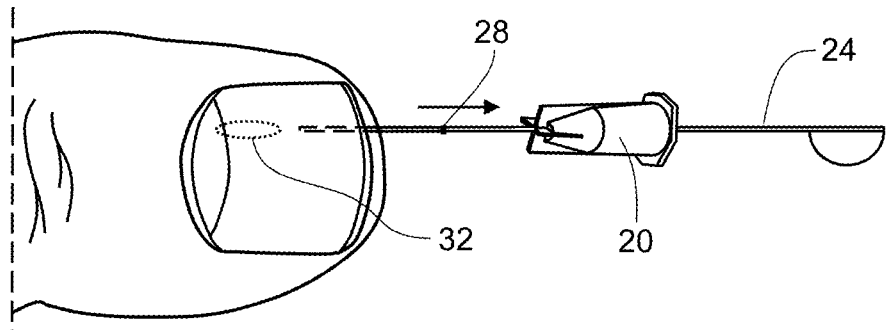

FIG. 1D illustrates an optional step in the implantation process. In this optional step, the needle, after inserting such that the indicator mark is aligned with the hyponychium and prior to depositing the composition, is withdrawn to a region between the distal edge of the lunula and the hyponychium. More particularly, the needle is withdrawn a distance of 0.5-5 mm, alternatively a distance of 0.5-4 mm, or 0.75-4 mm or 1-4 mm, to create a space 32 between the nail plate and the nail bed. The composition is then deposited into the space created by insertion of the needle. When the composition is a solution, liquid, or semi-solid, the composition may be deposited as the needle is withdrawn (retrograde injection or insertion). Depositing the composition into the space created by the needle/cannula reduces the force required to deposit the composition.

Figure 1E:
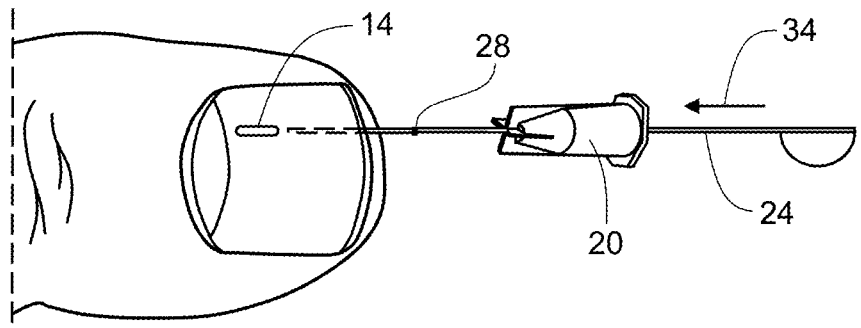
Figure 1F:
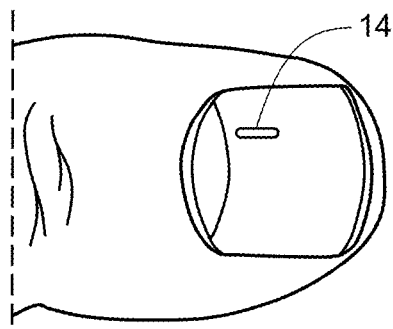

Then, as shown in FIG. 1E, stylet 24 is engaged to move in a direction shown by arrow 34, from the proximal end of the needle to the distal tip of the needle, to deposit composition 14 from the needle into the nail bed or into a subungual space between the nail plate and the nail bed, just distal to the lunula. The needle is then removed, as shown in FIG. 1F, leaving the composition in the nail unit.

Figure 2A:
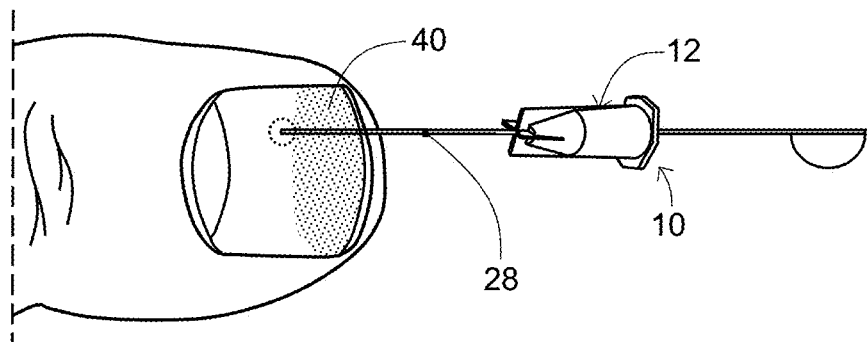
FIGS. 2A-2F illustrate another procedure for inserting an implant in accord with another embodiment.

Another embodiment of the implantation process is shown in FIGS. 2A-2F. Elements in FIG. 2 that are similar to elements in FIG. 1 are given the same numerical indicator for convenience. In the embodiment of FIG. 2, the location of the infection in the nail unit, rather than the lunula, is used as a guide for determining the indicator mark. It will further be appreciated that a further location on the nail plate may be used as a guide for determining the indicator mark. This approach is useful, for example, if the infection, or other disease or disorder, makes the lunula or other part of the nail bed not visible or having limited visibility, however, use of this approach is not so limited. With reference to FIG. 2A, a human finger and nail unit are shown, where the nail unit is infected with a fungus. The fungus causes discoloration, thickening and/or disfiguring of the nail plate, as denoted at 40 in FIG. 2A. Device 10, comprised of an applicator 12 and a composition 14, is provided, and if initially provided in a package, is removed from the packaging.

Administration of the implant subungually comprises placing the needle on the top of the nail plate such that the distal tip of the needle is approximately aligned with or extends just beyond a proximal point of fungal infection in the nail, as illustrated in FIG. 2A. When aligning the distal tip with a proximal point of fungal infection in the nail, the needle is placed on the top (or exterior surface) of the nail plate approximately one-third of the way across the nail unit, as depicted in FIG. 2A. Stated alternatively, the needle is placed on the exterior nail plate in a region defined by a longitudinal (intending a line extending from the free margin or distal edge of the nail plate to the eponychium) midline of the nail plate and a lateral nail fold—the "needle placement line." In one embodiment, the needle placement line is in the region defined by the longitudinal midline and a lateral nail fold where the radius of curvature is greatest. Upon correct placement of the needle, an indicator mark 28 along the needle shaft where it meets the hyponychium is noted. It will be appreciated that administration of the implant subungually may be accomplished without prior marking of the needle or cannula, especially where the nail unit allows sufficient visibility for subungual insertion. It will further be appreciated that other methods of visualizing the cannula and/or needle may be used including, but not limited to ultrasound and x-ray imaging.

Figure 2B:
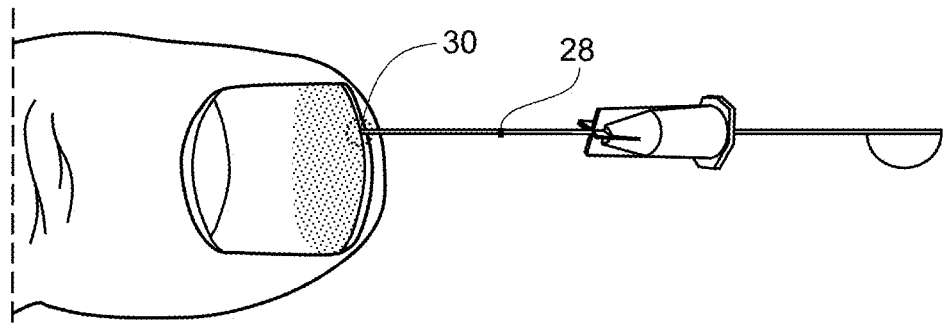
Figure 2C:
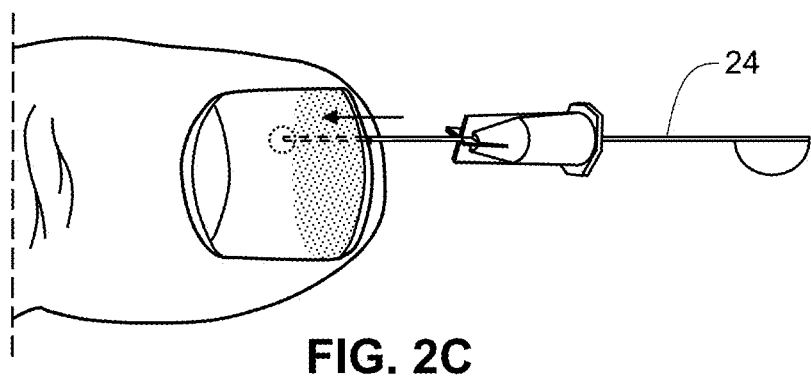

With reference to FIG. 2B, the needle is placed at a desired insertion point, indicated at 30 in FIG. 2B. The insertion point, in one embodiment, is at the level of the hyponychium along the needle placement line. This is illustrated in FIG. 2B, where the distal tip of the needle is positioned at the hyponychium along the needle placement line (see in FIG. 2A). As seen in FIG. 2C, the distal tip of the needle is inserted past the hyponychium, under the nail plate and into the subungual space between the nail plate and the nail bed. The needle is inserted until the indicator mark 28 is aligned with the hyponychium (FIG. 2C). In some patients, the disease or disorder such as an infection results in onycholysis, creating a space in the nail unit where the composition can be placed. In other patients, subungual debris is present, and debridement of the subungual debris creates a path or space for insertion and placement of a composition. Accordingly, the method described herein contemplates identifying for an individual patient the optimal insertion point of the needle, placement of the composition into the nail bed or a subungual space, and the composition. In some patients, the desired insertion point is at the point of greatest radius of curvature in the region defined by the longitudinal midline of the nail plate and a lateral nail fold. In other patients, the desired insertion point is in the region defined by the longitudinal midline of the nail plate and a lateral nail fold where onycholysis has occurred or where subungual debris has accumulated and can be removed.

Figure 2D:
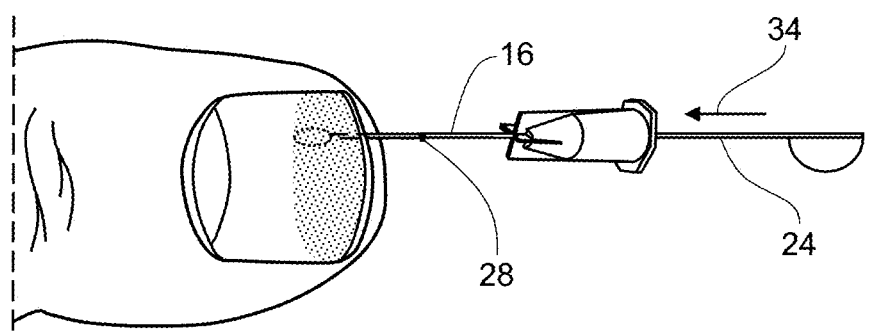
Figure 2E:
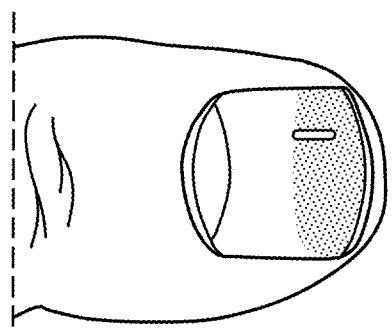

Then, as shown in FIG. 2D, stylet 24 is engaged to move in a direction shown by arrow 34, from the proximal end of the needle to the distal tip of the needle, to deposit composition 14 from the needle into the nail bed or into a subungual space between the nail plate and the nail bed, with a proximal edge of the composition at the approximate proximal edge of the site of infection. In another embodiment, the composition is deposited from the needle into the nail bed or into a subungual space without the use of a stylet. In one embodiment, the composition is deposited by pushing or injecting the composition through the needle to the desired site. The needle is then removed, as shown in FIG. 2E, leaving the composition in the nail unit at the desired location.

Figure 2F:
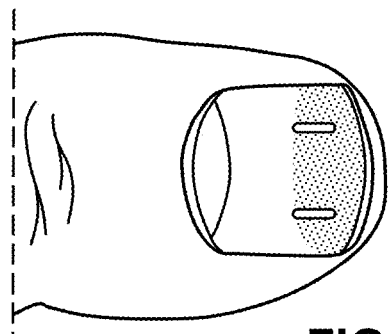

It will be appreciated that the steps described above for implantation of a composition subungually can be repeated to deposit a second composition and, if desired, subsequent compositions in the nail unit. It will further be appreciated that the second and any subsequent compositions may be the same or different than the first composition deposited. FIG. 2F depicts an infected nail unit with two solid compositions or implants. It will further be appreciated that, depending on the degree of onycholysis and/or subungual hyperkeratosis, where present, a fanning technique may be used to expand the space into which the composition is dispensed. It will also be appreciated that after the implantation procedure, pressure or a temperature treatment can be applied to the treatment site.

Figure 3A:
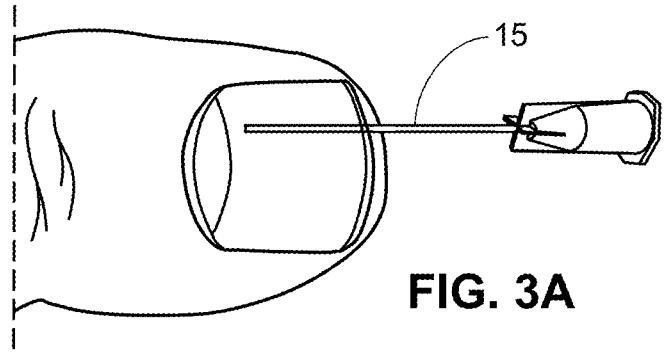
FIGS. 3A-3D illustrate another procedure for inserting an implant in accord with another embodiment.
Figure 3B:
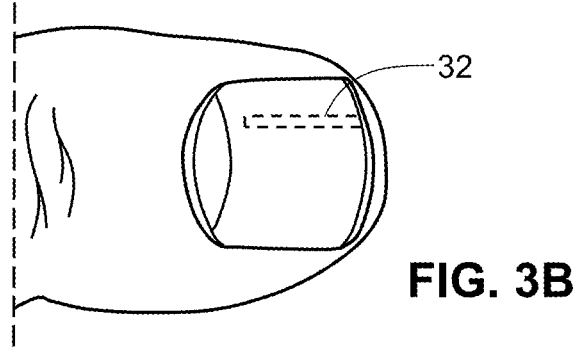
Figure 3C:
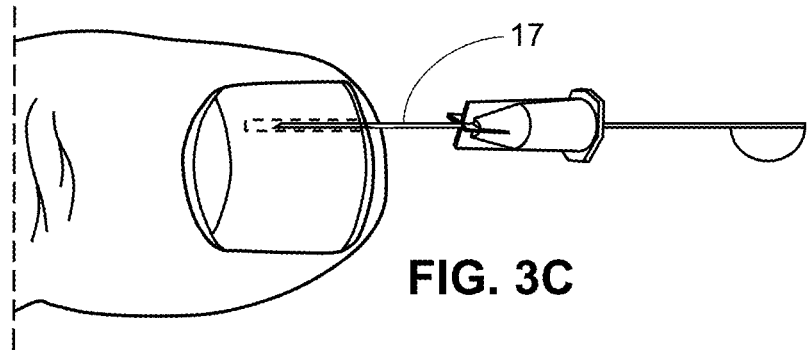
Figure 3D:
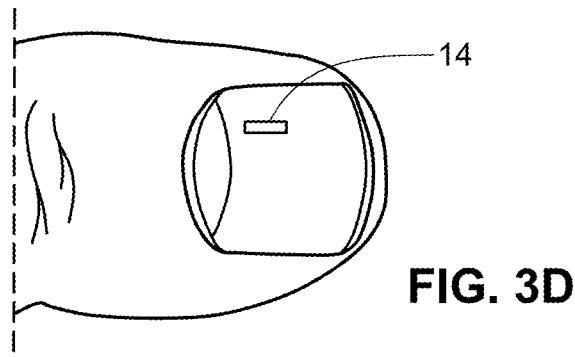

In one embodiment as shown in FIGS. 3A-3D, a cannula is used to create a subungual channel into which the active agent may be delivered. As shown in FIG. 3A, a blunt or rounded cannula is subungually inserted to create, define, or enlarge a subungual channel into which the composition may be administered. The cannula 15 is inserted into the subungual space as described above for the needle. The cannula is removed leaving a space or channel 32 in the subungual space (FIG. 3B). Using a cannula with a blunt tip or end may be useful to minimize or reduce pain and trauma as compared to subungual insertion of a needle. A needle or cannula 17 having the same or a finer gauge is then inserted into the channel 32 formed by the cannula 15 (seen in FIG. 3C). The needle may be inserted further into the subungual space than the depth of the channel if desired. The composition, product or implant 14 is administered into the channel 32 created by the blunt end cannula with the needle and the needle is removed (FIG. 3D). In another embodiment a liquid or semi-solid composition may be administered from an opening in the cannula. It will be appreciated that where a composition is administered from the cannula, administration of a same or different composition may be administered from a needle as described above. Although the composition may be administered as the cannula is inserted, it is preferable for the composition to be administered as the cannula is withdrawn (e.g. in retrograde fashion) to facilitate deposition of the composition with the cannula. The presence of a space in advance of the cannula/needle distal end avoids exertion of additional force or pressure to expel the composition from the cannula/needle. Administration of the composition from the cannula may further be in addition to administration of the same or a different composition from the needle.

As the cannula has a blunt end, it can be larger (lower gauge number) than the needle while minimizing or reducing pain and/or trauma. In an embodiment, the cannula and needle have the same gauge. In another embodiment, the needle has a finer (higher gauge number) than the cannula used to create, define or enlarge the subungual channel.

The methods described herein provide an approach for treatment that is individualized for each patient. As described above, for each individual patient the optimal insertion point of the needle is determined, based on condition of the nail and extent of disease or infection. In some patients, the insertion point is at the point of greatest radius of curvature in the region defined by the longitudinal midline of the nail plate and a lateral nail fold, and the depth of insertion is with respect to the distal edge of the lunula or with respect to the proximal edge of the disease or infection. In other patients, the desired insertion point is in the region defined by the longitudinal midline of the nail plate and a lateral nail fold where onycholysis has occurred or where subungual debris has accumulated and can be removed, and the depth of insertion is with respect to the proximal edge of the disease or infection or with respect to the distal edge of the lunula. The methods are also individualized in that the composition administered can be tailored, to be a solid, a semi-solid or a solution, or a combination thereof, as well as immediate release or extended release compositions, or a combination thereof. In the methods, the composition is desirably administered into a subungual space, and not into a tissue of the nail unit, in one embodiment.

It will also be appreciated that the nail unit and/or digit of the patient may be treated with one or more procedures, for example, with a disinfectant, an anesthetic to reduce pain, a hemostatic agent to decrease bleeding, or a keratolytic agent to facilitate device insertion/drug delivery. In one embodiment, the treatment procedure described herein is performed on a patient without anesthesia, local or systemic. Treatment with another procedure(s) may be done prior to the insertion procedure described herein, or may be done concurrent with the insertion procedure, as would be the case where the composition to be deposited subungually comprises a hemostatic agent or a keratolytic agent in addition to an antifungal agent. In one embodiment, a digital block is provided to the patient prior to inserting the cannula or needle past the hyponychium and under the nail plate.

The method of treatment and identification of an optimal site for depositing a composition subungually, described above, provides an unexpected advantage in reducing incidence of hematoma formation in the nail unit. It was found that the combination of the needle placement line and the indicator mark provide an accurate delivery protocol at a region in the nail unit most receptive to the implant. Insertion of the needle, and depositing the composition, along the line referred to above as the needle placement line, which is a line in a region defined by a longitudinal (intending a line extending from the free margin or distal edge of the nail plate to the eponychium) midline of the nail plate and a lateral nail fold, identifies a position in the nail unit that is more receptive to perturbation than, for example, at the midline of the nail. In some embodiments, identifying the needle placement line also includes identifying a point of greatest radius of curvature, of onycholysis and/or of the presence (and removal) of subungual debris, in the region for the needle placement line.

The nail plate may be intact, partially missing or otherwise compromised (e.g. damaged). In one embodiment, the nail of the subject suffering from a nail unit infection has an intact or uncompromised nail plate, and the process described above is performed. In another embodiment, the nail of the subject suffering from a nail unit infection or other disease or disorder is more than ⅔ compromised, by visual inspection, by the infection or other disease or disorder.

Figure 4A:
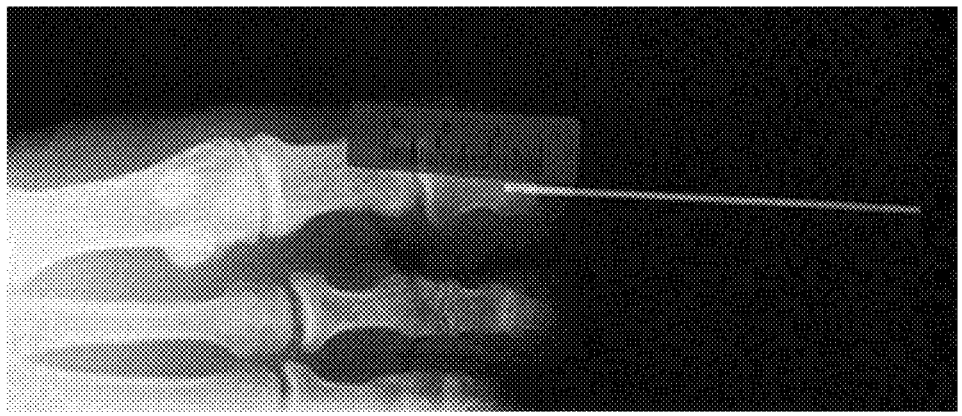
FIGS. 4A-4B are X-ray images showing subungual insertion of a cannula (FIG. 4A) and a needle (FIG. 4B).
Figure 4B:

The method of treatment and identification of an optimal site for depositing a composition subungually as described above provides an unexpected advantage of depositing the composition with low, minimal, reduced or no pain. In embodiments, the procedure may be performed with little or no anesthetic. As described in Example 3, a subject diagnosed with onychomycosis affecting 75% of the nail length underwent two procedures involving subungual insertion of a needle or subungual insertion of a needle preceded by subungual insertion of a blunt tip cannula. On the first day, a 25 gauge needle having a beveled tip was inserted into the subungual space. The patient reported pain during the procedure as a 0.6 on a scale of 0-10. Eighteen hours after the procedure, the subject reported no residual pain from the first procedure. On day 2, an 18 gauge blunt tip cannula was subungually inserted 6.5 mm (FIG. 4A). The cannula was withdrawn and an 18 gauge needle was inserted into the channel formed by the cannula (FIG. 4B). The subject reported pain from the second procedure as a 0 on the pain scale. Of note, the cannula and the needle as used in the second procedure was larger than the needle used in the first procedure (18 gauge vs. 25 gauge). Insertion of a 25 gauge needle resulted in slight pain. Insertion of a larger (18 gauge) cannula and needle resulted in no pain. Thus, use of a cannula results in minimal pain from the procedure as compared to subungual insertion of a needle, even for a larger diameter cannula. Nor did subungual insertion of a needle after the cannula result in increased pain as compared to insertion of the cannula alone. As described in Examples 4-9, the pain involved with insertion of a cannula and then insertion of a needle was similar or less than the pain involved with insertion of the cannula alone. As described in Example 6, even where the use of a cannula to create an initial channel in the subungual space requires anesthesia, subsequent access with a cannula/needle may be achieved without anesthesia and with significantly reduced pain. As described in Example 7, the methods described herein allow for treatment of nails that are difficult to treat or may not be treatable with other methods of treatment. Without being limited as to theory, the use of a blunt tip for the cannula may allow for subungual insertion of a larger instrument without trauma or minimal trauma to the nail bed. Further, subungual use of a blunt tip cannula followed by subungual insertion of a needle for deposition of a composition is relatively painless/incurs minimal pain.

A. Dosing Regimen

In another aspect, a dosing regimen for treating a disease or disorder of the nail unit is provided. In embodiments, a dosing regimen for treating an infection such as a bacterial or fungal infection is provided. In one particular embodiment, a dosing regimen for treating onychomycosis is provided. In other embodiments, a dosing regimen for treating psoriatic nail disease is provided. The regimen comprises administering subungually a first device and a second device, the first and second devices each comprised of a biodegradable polymeric matrix and an antifungal agent dispersed in the matrix. Then, a period of time is allowed to pass and a third device and optionally a fourth device is/are administered, the third device and optional fourth device comprised of a biodegradable polymeric matrix and a therapeutic or active agent such as an antifungal agent dispersed in the matrix. The period of time that passes achieves release of the therapeutic or active agent from the matrix at a rate to maintain a concentration of therapeutic or active agent in a substantial portion of the nail bed above the minimum inhibitory concentration; and the administering comprises depositing the devices at a position between a lateral nail fold and a longitudinal midline of the nail plate.

In one embodiment of the dosing regimen, the implantation procedure set forth in FIG. 1, FIG. 2, or FIG. 3 is followed, to deposit the desired number of devices or compositions in a space between the nail plate and the nail bed.

The period of time that lapses between administration of the first and second compositions and additional compositions can be about two weeks, four weeks, six weeks, eight weeks or twelve weeks. The period of time is determined by several factors, such as the condition of the patient, the extent of the disease or infection, and the properties of the composition. It is preferred that the composition is a controlled-release composition that provides release of one or more active ingredient(s) over a period of time, for example, at least about 2 days, or at least about 7 days, or over a period of at least about 10 days, or at least about 14 days, or at least about 30 days, or at least about 45 days, or over one month or more. Preferred embodiments include those that release an active ingredient over 2 months or more, or three months or more. The components in a controlled-release composition may be tailored according to the release time required, for example to vary the release period from about 1 month to about 6 months. In embodiments, the composition provides release of the one or more active ingredient(s) over a period of at least about 1-2 days, 1-7 days, 1-10 days, 1-14 days, 1-30 days, 2-7 days, 2-days, 2-14 days, 2-30 days, 7-10 days, 7-14 days, 7-30 days, 14-30 days, 30-45 days, or more. In other embodiments, the composition provides release of the one or more active ingredient(s) over a period of at least about one week, two weeks, three weeks, one month, six months or more. In further embodiments, the composition provides release of the one or more active ingredient(s) over a period of at least about 1 month, 2 months, 3 months, 4 months, 5 months, 6 months, 9 months, 12 months, or more. It will be appreciated that the period of release may be provided by administration of the further compositions.

In another embodiment, the compositions provide for immediate release of the therapeutic or active agent(s), such as an anti-fungal agent. In one embodiment, the agent is released from the composition within about 10 minutes-2 hours after administration, preferably within about 10 minutes-1 hour, or 10 minutes-30 minutes after administration. Subsequent immediate release compositions can be administered at any desired interval, and can also be administered in conjunction with compositions that provide for an extended release of the agent, where the immediate release composition and an extended release composition are administered at the same time or subsequent to each other.

The total dose delivered for the active agent may vary depending on such factors as the particular agent used and whether the composition is being administered for treatment or prophylaxis. For example, the active agent delivered to the tissues of the nail unit in a given administration may be between about 10 µg and about 1 mg, or between about 0.05 mg and about 0.5 mg. In some embodiments, the composition is a solid or semi-solid composition that comprises between about 0.25-1.0 mg, preferably between about 0.25-0.75 mg, more preferably between about 0.25-0.50 mg of an agent such as an anti-fungal agent. Determining the total dose of the active agent may be determined based on recommended or approved dosages and/or studies to determine the appropriate dose.

The ability of the nail plate to store a drug is known in the art. Thus, in an embodiment of the present treatment method, compositions are deposited periodically that take advantage of the ongoing presence of active ingredient in the nail plate, even after release of the active ingredient from the composition is complete. Subsequent treatment with additional compositions may be timed to account for the ongoing presence of active ingredient in the nail plate.

In another embodiment, the methods are used in combination with additional therapies for the treatment of diseases of the nail unit. For example, a controlled release composition or composition of the present method is deposited subungually or periungually and is used in combination with a topical treatment. Such combination treatments can be particularly advantageous when treatment of both the nail bed and nail plate are required, for example, in certain forms of onychomycosis. As an example, it is envisioned that the use of a topical lacquer containing terbinafine hydrochloride be combined with the use of a subungually deposited controlled release subungual or periungual composition containing terbinafine hydrochloride for the treatment of onychomycosis. In other embodiments, it is envisioned that oral compositions for systemic delivery of an active ingredient be combined with compositions for the treatment of various diseases of the nail unit, including onychomycosis and nail psoriasis. In other embodiments, it is envisioned that suitable conventional therapies as previously discussed herein for the treatment of the various diseases of the nail unit be used in combination with the compositions now to be described.

B. Composition Components

As mentioned above, a composition for use in the treatment method described herein may take varying forms, e.g., a solid, a semisolid, or a solution. The solution can be a dispersion, suspension or emulsion. The composition may be a non-temperature dependent phase change composition. The composition may also take the form of microparticles, nanoparticles, crystals, and the like, depending on such factors as the particular active agent used, the type of nail condition being treated, and the medical history of the patient. However, in all instances, the composition contains a drug load capable of delivering a therapeutically effective amount of an active agent to treat a nail unit condition. By "therapeutically effective amount" it is meant an amount of active agent effective to treat a nail unit condition. The compositions, in one embodiment, include an active agent and a biocompatible carrier or a matrix forming material that may be a biodegradable, bioerodible, or bioabsorbable polymer. The compositions may have any suitable form, and any suitable type of release, e.g., they may be configured for sustained release or immediate release.

When a solution, the composition is preferably an injectable liquid. Solutions with dissolved or dispersed active agent may be formulated to deliver a large amount of active agent in a small volume, e.g., about 10 µL to about 250 µL or about 50 µL to about 100 µL. Generally, any solvent that is suitable for injection into tissue may be used. Solvents that may be beneficial for these solutions include without limitation, water, oils, such as silicone oil, sesame oil, corn oil and the like, ethanol, dimethyl sulfoxide (DMSO), N-methylpyrrolidone, or N,N-dimethylacetamide, polyethylene glycol 400 or polyethylene glycol 600. A surfactant may be beneficial for use with these solutions, e.g., a polysorbate such as polysorbate 80 (Tween-80). Adjustment of the pH of the solution may also be beneficial to enhance the solubility of the active. For active agents that exist in a salt form, the liquid formulation may comprise the salt form of the active and or the free base form of the active. Where the active agent may exist in a liquid form at room temperature, e.g., the un-ionized or free base form of terbinafine, the liquid composition may comprise up to and including 100% active agent.

In one embodiment, the active is preferably present in about 0.1 wt. % to about 50 wt. % of the solution composition. In other embodiments, the active is preferably present in about 0.1 wt. % to about 30 wt. %, more preferably from about 1 wt. % to about 30 wt. %, even more preferably from about 5 wt. % to about 25 wt. %, of the composition. In other embodiments, the composition, whether a solution or semi-solid, comprises between about 0.1-25 percent by weight of the active such as an anti-fungal agent, more preferably between about 0.5-20 or 0.5-5 percent by weight.

A composition in the form of a solution can generally be injected with a needle or cannula having a gauge of 18 or 19 or higher, more preferably 20 or higher, or 25 or higher, or 30 or higher. In one embodiment, the needle or cannula has a gauge of at least about 18-30 or higher. In other embodiments, the needle or cannula has a gauge of at least about 18-25 or higher. The gauge of the needle or cannula is selected such that the composition may flow through the needle or cannula into the subungual or periungual space, while at the same time minimize local trauma and discomfort in the subject. In one, non-limiting embodiment, an 18 gauge blunt tip cannula is inserted into the subungual space which creates a channel or space in the subungual space. The cannula is removed and an 18 gauge or 25 gauge needle is inserted at least partially into the channel or space created by the cannula. A composition is inserted into the channel or space and the needle is withdrawn.

In a preferred embodiment, the solution composition remains substantially deposited subungually or periunguaIly upon withdrawal of the needle or cannula. In another embodiment, the composition to be injected comprises a flowable gel, a suspension or a solution, comprised of the active agent and a liquid carrier, such as an oil or other hydrophobic solvent. In one embodiment, the oil is a silicone oil.

A solid composition may be comprised of only one or more drug or agent or may be comprised of one or more drug or agent dispersed in a biocompatible carrier or matrix material. The carrier or matrix material may be any biocompatible polymeric or nonpolymeric material. The biocompatible materials may also be biodegradable, bioerodible, or bioabsorbable, and some examples are listed below.

The solid compositions may include at least about 30% by weight of an active agent, at least about 50% by weight of an active agent, or in some instances, at least about 75% by weight of an active agent. In one embodiment, the composition is comprised of a biodegradable polymer. In another embodiment, the biodegradable implant is a solid implant comprised of a polymer having a melting temperature (Tm) greater than the temperature of the nail bed. In one embodiment, the composition is a "non-temperature dependent phase change composition," which refers to a composition that does not undergo a phase transition, e.g., a transition between the solid, semi-solid, and liquid phases, due to a change in temperature.

In one embodiment, the composition is a solid and comprises at least one active agent generally dispersed in a biocompatible carrier or matrix material. The carrier or matrix material may be any biocompatible polymeric or nonpolymeric material. The biocompatible materials may also be biodegradable, bioerodible, or bioabsorbable. As used herein, the term "biocompatible" refers to a carrier or matrix material that does not cause significant tissue irritation at the target site. The term "biodegradable" refers to carrier or matrix material that degrades over time by enzymatic or hydrolytic action, or other mechanism at the target site. By "bioerodible," it is meant that the carrier or matrix material erodes or degrades over time by contact with surrounding tissue fluids, through cellular activity or other physiological degradation mechanisms. By "bioabsorbable," it is meant that the carrier or matrix material breaks down and is absorbed by a cell, tissue, or other physiologic mechanism. In another embodiment, the composition is a solid and comprises at least one active agent coated by a biocompatible material. The coating material may be a material as described with reference to a carrier or matrix material or may be a biocompatible coating material as known in the art.

Selection of the composition components will vary depending on the desired release kinetics, formulation constraints, the nature of the condition to be treated, and the like. Polymer characteristics that are considered include, but are not limited to, compatibility with the active agent of interest and processing temperatures. The biocompatible polymer matrix usually comprises less than about 70, less than about 65, less than about 60, less than about 55, less than about 50, less than about 45, less than about 40, less than about 35, less than about 30, less than about 25, less than about 20, less than about 15, less than about 10, less than about 5, less than about 2.5, or about zero weight percent of the composition. In one variation, the biocompatible polymer comprises about zero percent by weight of implant composition. In another variation, the biocompatible polymer matrix comprises about 30% by weight of the implant.

Biocompatible polymers may be employed include, but are not limited to, poly(lactide)s; poly(glycolide)s; poly(lactide-co-glycolide)s; poly(lactic acid)s; poly(glycolic acid)s; poly (lactic acid-co-glycolic acid)s; poly(caprolactone)s; poly (orthoester)s; poly(phosphazene)s; poly(phosphoester)s; poly(hydroxybutyrate)s or copolymers including poly(hydroxybutyrate); poly(lactide-co-caprolactone)s; polycarbonates; polyesteramides; polyanhidrides; poly(dioxanone)s; poly(alkylene alkylate)s; copolymers of polyethylene glycol and a polyorthoester; biodegradable polyurethanes; poly (amino acid)s; polyetheresters; polyacetals; polycyanoacrylates; polyvinyl alcohol); poly(oxyethylene)/poly(oxypropylene) copolymers; or blends, copolymers, and mixtures thereof.

In one variation, copolymers of glycolic and lactic acid are used. The percent of each monomer in poly(lactic-co-glycolic)acid (PLGA) copolymer may be 0-100%, about 15-85%, about 25-75%, or about 35-65%. If desired, a 50/50 PLGA copolymer may be employed. End-capped (e.g., acid-capped or ester-capped) or uncapped PLGA, or a combination of the two forms may also be used.

Other components that may be used alone or in combination with the biocompatible polymers mentioned above to form an implant, include, but are not limited to, polyethylene glycol (PEG), vitamin E and its derivatives, dimethyl sulfone (MSM), carbamide, and blends and mixtures thereof.

In one embodiment, the composition is comprised of a polyethylene glycol with a molecular weight of between 1,000-8,000 Daltons, more preferably between 2,000-5,000 Daltons, still more preferably of between 2,500-4,000 Daltons, and in one embodiment is 3,500 Daltons. In these embodiments, the composition may be comprised of one or more active agents such as an antifungal agent distributed within a polyethylene glycol. The composition may comprise less than about 40 weight percent polyethylene glycol, preferably less than about 30 weight percent polyethylene glycol, still more preferably 25 weight percent or less polyethylene glycol. The composition may comprise at least about 60 weight percent, at least about 65 weight percent, at least about 70 weight percent, at least about 75 weight percent or at least about 80 weight percent of the active agent. In one embodiment, the composition comprises between about 70-80 weight percent active agent, alternatively, between about 65-85 weight percent active agent.

When formulated as a semisolid, the composition will usually be a semisolid emulsion, a gel, a cream, an ointment, a lotion or a paste. Semisolid emulsions are either oil-in-water or water-in-oil emulsions. Gels are typically suspension-type systems. Single-phase gels contain gelling agents distributed substantially uniformly throughout the carrier liquid, which is typically aqueous, but which may also contain an alcohol and, optionally, an oil. Examples of gelling agents that may be used include, but are not limited to, crosslinked acrylic acid polymers such as the carbomer family of polymers, e.g., carboxypolyalkylenes that may be obtained commercially under the CARBOPOL trademark; hydrophilic polymers such as polyethylene oxides, polyoxyethylene-polyoxypropylene copolymers, and polyvinylalcohol; cellulosic polymers such as hydroxypropyl cellulose, hydroxyethyl cellulose, hydroxypropyl methylcellulose, hydroxypropyl methylcellulose phthalate, hydroxypropyl methylcellulose acetate-succinate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof. Pastes are semisolid dosage forms in which the active agent is suspended in a suitable base. Depending on the nature of the base, pastes are divided between fatty pastes or those made from single-phase aqueous gels. The base in a fatty paste is generally petrolatum, hydrophilic petrolatum or the like. The pastes made from single-phase aqueous gels generally incorporate carboxymethylcellulose or the like as a base.

The compositions may also take the form of a semi-solid or a liquid that solidifies after implantation. Solidification may occur due to temperature changes after implantation or to diffusion of a solvent out of the composition into the surrounding tissue.

In general, the volume of the composition delivered will be small. For example, when solutions are delivered, volumes less than about 500 µL, less than about 400 µL, less than about 300 µL, less than about 200 µL, or less than about 100 µL may be implanted (e.g., by injection). For solids, generally less than about 100 µL, and in some instances, less than about 10 µL, may be used. In some variations, volumes between greater than about 0 µL and about 5 µL may be employed. Given these small volumes, fine gauge needles or cannulas will generally be used to deliver the compositions. For example, 19 gauge, 21 gauge, 23 gauge, 25 gauge, 26 gauge, 27 gauge, 28 gauge, 29 gauge, or 30 gauge needles or cannulas may be used.

The compositions described here may be delivered in any size, shape, and/or volume compatible with the site of implantation, as long as they have the desired drug loading and release kinetics, and deliver an amount of active agent that is therapeutic for the intended nail condition. For example, the solid compositions may be formed as particles, sheets, discs, filaments, rods, and the like. The solid compositions may be formed to have volumes between greater than 0 $mm^3$ to about 20 $mm^3$, between greater than about 0 $mm^3$ to about 10 $mm^3$, or between about 1 $mm^3$ to about 20 $mm^3$. In some instances, the solid compositions may be formed to have a volume of greater than about 0 $mm^3$ to about 1 $mm^3$. However, in some variations, the volume may be greater than 20 $mm^3$.

As the subungual space is limited and may be at least partly occluded, consideration may be given to the volume dispensed and the presence or concentration of volatile and/or irritating excipients. The degree of disease presentation (e.g. extent of onycholysis and/or subungual hyperkeratosis, and whether the nail plate is intact or complete) may affect the volume of composition that is delivered. Additionally, volume of composition that may be delivered may be affected or controlled by other treatment to the nail unit or other preparation of the nail unit. Exemplary treatments and/or preparations that may affect the volume of composition that may be delivered include, but are not limited to, preparation of the nail unit by the patient or health care professional (e.g. debridement, cutting back of the nail, pretreatment with keratolytic agent such as urea or salicylic acid).

The volume of a liquid or semi-solid product or composition may be limited by the volume of a channel created by insertion of the needle and/or cannula. The channel created by the cannula/needle and the resulting volume made available for administration of the composition may be estimated by considering the outside diameter of the cannula or needle and the depth of insertion past the hyponychium. The volume for a solid product or composition may be limited by the inside diameter of the cannula/needle as the solid must fit within the cannula/needle. Further, the volume for a solid product or composition may be limited by the length of the solid product or composition. The length of the solid product or composition may be selected based on the length of the nail plate and/or the extent of disease, among other factors. For Table 1, a length of the solid product or composition of about 4-6 or 4-8 mm was considered. The volume of a solid product or composition may further be limited by the depth of insertion and/or the length of the cannula/needle. The nail plate is typically about 15 mm or less.

Table 1 shows the approximate volume of space created by insertion of a cannula (or needle) having a gauge of 30, 25, 21, and 18. In some embodiments, the volume of agent delivered may be determined, approximated, or limited by the volume of space of the cannula or needle. It will be appreciated that the depth of insertion may be varied depending upon the volume of agent that is to be delivered.

TABLE 1

Volume of Space ($mm^3$) Created According to Gauge of Cannula and Depth of Insertion

| Gauge of Cannula | Depth of Insertion (mm) | | | | | | | | |
|---|---|---|---|---|---|---|---|---|---|
| | 4 | 5 | 6 | 7 | 8 | 9 | 10 | 11 | 12 |
| 30 | 0.30 | 0.38 | 0.46 | 0.53 | 0.61 | 0.68 | 0.76 | 0.84 | 0.91 |
| 25 | 0.83 | 1.04 | 1.24 | 1.45 | 1.66 | 1.87 | 2.07 | 2.28 | 2.49 |
| 21 | 2.11 | 2.63 | 3.16 | 3.69 | 4.21 | 4.74 | 5.27 | 5.79 | 6.32 |
| 18 | 5.07 | 6.33 | 7.60 | 8.87 | 10.13 | 11.40 | 12.67 | 13.93 | 15.20 |

Table 2 shows the approximate volume of an implant that is positionable within a cannula (or needle) having a gauge of 30, 25, 21, and 18.

TABLE 2

Volume of Implant ($mm^3$) According to Gauge of Needle and Length of Implant

| Gauge of Needle | Implant Length (mm) | | | | |
|---|---|---|---|---|---|
| | 4 | 5 | 6 | 7 | 8 |
| 30 | 0.07 | 0.08 | 0.10 | 0.12 | 0.13 |
| 25 XXTW | 0.45 | 0.57 | 0.68 | 0.79 | 0.91 |
| 21 | 0.79 | 0.99 | 1.18 | 1.38 | 1.58 |
| 18 | 2.14 | 2.67 | 3.21 | 3.74 | 4.28 |

It will be appreciated that the length of the implant may be varied to adjust the volume of the implant. Where the agent is a liquid or semi-solid, the amount of agent may be varied by adjusting the length of the cannula or needle that contains the agent. The volume of agent may be also be varied by using a larger or finer gauge cannula or needle.

As used herein, the terms "active agent", "therapeutic agent", "agent", and "drug" are used interchangeably and refer to any substance used to treat conditions of the nail. The active agents generally used in the compositions described here include, an anti-infective agent, such as antibacterial agents, antifungal agents, antiviral agents, and antiseptics. Examples of antifungal agents that may be incorporated into the composition include, in some embodiments, azole derivatives and fungicidal allylamines. The azole derivatives include ketoconazole, fluconazole, itraconazole, voriconazole, bifonazole, clotrimazole, miconazole, econazole, butoconazole, oxiconazole, sulconazole, terconazole, liarozole, irtemazol, efinaconazole, and luliconazole, as well as substituted derivates of these such as substituted thiazole, thiadiazole, and oxadiazole. Allylamines include, without limitation, naftifine, terbinafine salts, and terbinafine free base. Other anti-fungal agents include butenafine, tavaborole, tolnaftate, amorolfine; ciclopirox; flucytosine; griseofulvin; haloprogrin; potassium iodide sodium pyrithione; undecylenic acid; polyene antifungal antibiotics such as amphotericin B and nystatin; antifungal organic acids such as benzoic acid, salicylic acid, propionic acid, caprylic acid; and derivatives and combinations thereof. Further, commercial antifungal formulations or formulations for treatment of skin infections (e.g. tinea pedis) may be used for subungual delivery using the methods described herein. Commercial formulations include a variety of solutions and semi-solid (creams, ointments, etc.). In embodiments, the concentration of active agent and/or excipients may be adjusted for subungual delivery. Exemplary commercial formulations include, but are not limited to butenafine HCl 1% (cream, solution), clotrimazole combinations (cream, solution, gel), ciclopirox olamine 1% (cream or lotion), ketoconazole (cream, liquid), miconazole nitrate, mycostatin (cream), naftifine HCl 1% (cream, gel), oxiconazole nitrate (cream), terbinafine HCl 1% (cream, solution, spray, patch), terbinafine once daily (Lamisil Once), tolnaftate (cream, spray, liquid), sulconazole (cream, solution). Further products for topical treatment of the nail unit that may be used for subungual delivery include ciclopirox/Penlac, amorolfine/Loceryl, efinaconazole, luliconazole 10% (solution), NM100060 and tavobarole.

The choice of a particular antifungal agent will be readily apparent to those skilled in the art. For example, dermatophyte onychomycosis may be treated by an antifungal agent effective against dermatophytes, such as terbinafine. As another example, a case of onychomycosis of uncertain fungal etiology may be treated with a broad-spectrum antifungal agent effective against dermatophytes, nondermatophyte molds, and yeasts, such as itraconazole.

In other embodiments, the active agents generally used in the compositions described herein include antipsoriatic agents generally and agents for use in treating psoriatic nail disease in particular. Examples of antipsoriatic agents that may be incorporated into the composition include, in some embodiments, corticosteroids, salicylic acid, vitamin D analogs and derivatives, retinoids and derivatives thereof, antimetabolites, and immunosuppressants/calcineurin inhibitors. Suitable corticosteroids include any of the topical corticosteroids such as betamethasone dipropionate, clobetasol, and triamcinolone acetonide. Suitable vitamin D analogs include, but are not limited to calcipitriol, calcipotriene, tacalcitol, and calcitriol. Suitable retinoids or retinoid derivatives include, but are not limited to tazarotene. One suitable antimetabolite is 5-fluorouracil. One suitable immunosuppressant is pimecrolimus.

When the composition is in the form of a solid, to form an implant, the active agent may constitute from greater than about 30%, from greater than about 35%, from greater than about 40%, from greater than about 45%, from greater than about 50%, from greater than about 55%, from greater than about 60%, from greater than about 65%, from about 70%, from greater than about 75%, from greater than about 80%, from greater than about 85%, from greater than about 90%, from greater than about 95%, or about 100% by weight of the implant. In one variation, the active agent comprises greater than 100% of the implant. Drug loading may be varied to achieve high initial drug release (burst release). In one embodiment, the active agent comprises about 70% by weight of the implant. In one embodiment, the antifungal agent is terbinafine hydrochloride or is terbinafine free base. In another embodiment, the agent is released by erosion or degradation of the polymer over a period of at least about 2 weeks, alternatively over a period of at least about 4 weeks.

In one embodiment, the agent is released to provide an initial burst of agent followed by a period of extended release of agent. In one embodiment, the period of extended release comprises at least about 10 days, preferably at least about 2 weeks, more preferably at least about 4 weeks.

In yet another embodiment, the active ingredient used in the methods and implants may comprise more than one active ingredient. For example, the active ingredient may comprise a combination of active ingredients that demonstrate an additive or synergistic effect. Methods to determine such combinations are well-known to those of skill in the art.

III. Examples

The following examples are illustrative in nature and are in no way intended to be limiting.

Example 1

Exemplary Solid Implant

A terbinafine implant is made by mixing terbinafine HCl 1 and polyethylene glycol, molecular weight 3350 Daltons, in a ratio of 80:20 respectively (total weight of the mixture is 20 g). The mixture is filled into a batch extruder and heated for one hour at 100° C. The melt is then extruded through a circular orifice to create a filament having a diameter of about 0.4 mm. From the filament, various length subunits are cut to form individual implants.

Example 2

Exemplary Solution

An aqueous solution of terbinafine HCl is reacted with sodium hydroxide at a pH of 7.5 to 13.0 to form the free base form of the drug. The free base form is separately isolated and mixed with a silicon oil to form a flowable composition that can be administered as an implant.

Example 3

Subungual Insertion of Cannula and Needle

A subject diagnosed with onychomycosis and exhibiting onycholysis/subungual hyperkeratosis of the distal-central area of the hallux nail underwent subungual insertion of a 25 gauge needle on day one. The nail length of the hallux was 12 mm and 9 mm of the nail was involved. The needle was inserted into the space between the nail bed and the nail plate created by the onycholysis in the direction from the hyponychium toward the lunula without anesthesia. Insertion was between the midline of the nail plate and the lateral nail fold. The subject reported slight pain during the procedure as a 0.6 on a pain scale of 0 to 10 (0 being no pain, 10 being the worst pain). At 18 hours post-procedure, the subject reported pain as a zero on the pain scale.

On day two, the subject underwent a second procedure on the same nail. An 18 gauge cannula with a blunt tip was subungually inserted 6.5 mm to define a subungual channel. The X-ray image as shown in FIG. 4A shows placement of the cannula in the subungual space. The cannula was withdrawn and an 18 gauge needle was inserted 8 mm into and beyond the channel. The X-ray image as shown in FIG. 4B shows placement of the needle in the subungual channel. The entire second procedure was performed without anesthesia. The patient reported pain during the second procedure as a zero on the pain scale. Insertion of a 25 gauge needle on the first day resulted in slight pain. Insertion of a much larger 18 gauge blunt tip cannula followed by insertion of an 18 gauge needle resulted in no pain. Thus, insertion of an 18 gauge cannula/needle was performed without causing pain.

Example 4

Subungual Insertion of Cannula and Needle

A subject was diagnosed with onychomycosis and exhibited onycholysis/subungual hyperkeratosis primarily of the lateral aspect of the hallux nail. The nail length was 13 mm and 10 mm of the nail was involved. The subject underwent subungual insertion of an 18 gauge cannula on day one. The needle was inserted into the space between the nail bed and the nail plate created by the onycholysis/subungual hyperkeratosis in the direction from the hyponychium toward the lunula without anesthesia. Insertion was between the midline of the nail plate and the lateral nail fold. The subject reported pain during the procedure as a 3.1 on the pain scale. At 18 hours post-procedure, the subject reported pain as a 2.2 on the pain scale.

On day two, the subject underwent a second procedure on the same nail. An 18 gauge cannula with a blunt tip was subungually inserted 6.5 mm to define a subungual channel. The cannula was withdrawn and an 18 gauge needle was inserted 9 mm into and beyond the channel. The entire second procedure was performed without anesthesia. The patient reported pain during the second procedure as a 4.4 on the pain scale.

Example 5

Subungual Insertion of Cannula and Needle

A subject was diagnosed with onychomycosis and exhibited subungual hyperkeratosis of the central and lateral aspects of the distal ¾+ of the hallux nail. The nail length was 12.5 mm and 9 mm of the nail was involved. The subject underwent subungual insertion of an 18 gauge cannula on day one without anesthesia as described in Example 4. The subject reported pain during the procedure as a 0.4 on the pain scale. At 18 hours post-procedure, the subject reported pain as a 0 on the pain scale.

On day two, the subject underwent a second procedure on the same nail. An 18 gauge cannula with a blunt tip was subungually inserted 6 mm to define a subungual channel. The cannula was withdrawn and an 18 gauge needle was inserted 7 mm into and beyond the channel. The entire second procedure was performed without anesthesia. The patient reported pain during the second procedure as a 0.2 on the pain scale.

Example 6

Subungual Insertion of Cannula and Needle

A subject was diagnosed with onychomycosis and exhibited a thickened nail plate and very dense subungual hyperkeratosis of the hallux nail. The nail length was 13 mm with the entire nail, including matrix/lunula involved. The subject underwent subungual insertion of an 18 gauge cannula on day one as described in Example 4. The subject reported pain during the procedure as a 9 on the pain scale and was administered a digital block anesthesia. At 18 hours post-procedure, the subject reported pain as a 6.2 on the pain scale.

On day two, the subject underwent a second procedure on the same nail. An 18 gauge cannula with a blunt tip was subungually inserted 5.5 mm. The cannula was withdrawn and an 18 gauge needle was inserted 11 mm into and beyond the channel. The entire second procedure was performed without anesthesia. The patient reported pain during the second procedure as a 4.2 on the pain scale. The example demonstrates that in patients with a thick adherent nail and dense subungual hyperkeratosis involving all or most of the nail, creating of an initial channel with a cannula may require the use of an anesthetic procedure to minimize pain. Once the channel has been formed, subsequent access with a cannula/needle may be achieved without anesthesia and with significantly reduced pain.

Example 7

Subungual Insertion of Cannula and Needle

A subject was diagnosed with onychomycosis and exhibited prominent subungual hyperkeratosis of both lateral aspects of the hallux nail. The nail length was 12 mm and 8 mm of the nail was involved. The subject underwent subungual insertion of an 18 gauge cannula on day one without anesthesia as described in Example 4. The subject reported pain during the procedure as a 1 on the pain scale. At 18 hours post-procedure, the subject reported pain as a 0 on the pain scale.

On day two, the subject underwent a second procedure on the same nail. An 18 gauge cannula with a blunt tip was subungually inserted 9.5 mm to define a subungual channel. The cannula was withdrawn and an 18 gauge needle was inserted 11.5 mm into and beyond the channel. The entire second procedure was performed without anesthesia. The patient reported pain during the second procedure as a 1.1 on the pain scale. Use of a cannula prior to insertion of the needle resulted in similar pain for subungual insertion of a cannula alone.

Onychomycosis exhibiting lateral edge nail involvement has been reported to have a poor prognosis in response to systemic antifungal agents, presumably due to poor drug access to the site(s) of infection. Patients presenting with this pattern of involvement are also frequently excluded from studies with topical antifungal agents. This example demonstrates the ability of a cannula/needle to access infection sites directly with minimal pain by circumventing systemic delivery and circumnavigating the nail plate.

Example 8

Subungual Insertion of Cannula and Needle

A subject was diagnosed with onychomycosis and exhibited yellow streaks and onycholysis/hyperkeratosis primarily in the distal-central aspect of the hallux nail. The nail length was 9 mm and the entire nail length was involved. The subject underwent subungual insertion of an 18 gauge cannula on day one without anesthesia as described in Example 4. The subject reported pain during the procedure as a 1 on the pain scale. At 18 hours post-procedure, the subject reported pain as a 1 on the pain scale.

On day two, the subject underwent a second procedure on the same nail. An 18 gauge cannula with a blunt tip was subungually inserted subungually to the midline 7 mm to define a subungual channel. The cannula was withdrawn and an 18 gauge needle was inserted 8 mm into and beyond the channel. The entire second procedure was performed without anesthesia. The patient reported pain during the second procedure as a 0.1 on the pain scale. Although the adherence of the nail plate to the bed is typically very tight in the midline area of the nail, the onycholysis and subungual hyperkeratosis allows for cannula/needle insertion with minimal pain.

Example 9

Subungual Insertion of Cannula and Needle

A subject was diagnosed with onychomycosis and exhibited moderate onycholysis/subungual hyperkeratosis of the hallux nail. The nail length was 14 mm and 12 mm of the nail was involved. The subject underwent subungual insertion of an 18 gauge cannula on day one without anesthesia as described in Example 4. The subject reported pain during the procedure as a 0.1 on the pain scale. At 18 hours post-procedure, the subject reported pain as a 0.3 on the pain scale.

On day two, the subject underwent a second procedure on the same nail. An 18 gauge cannula with a blunt tip was subungually inserted 11.5 mm to define a subungual channel. The cannula was withdrawn and an 18 gauge needle was inserted 12.5 mm into and beyond the channel. The entire second procedure was performed without anesthesia. The patient reported pain during the second procedure as a 0.3 on the pain scale.

This example demonstrates that with the cannula/needle procedure described, subungual delivery even beyond the area of disease involvement may be achieved without anesthesia and with minimal pain.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A method for treating onychomycosis, comprising:
   determining an insertion point for insertion of an instrument subungually between a nail plate and a nail bed in a nail unit of a subject with onychomycosis;
   identifying a visible proximal edge of fungal infection in the nail unit of the subject; and
   administering, by insertion at the insertion point to deposit at approximately the visible proximal edge of fungal infection, a composition comprising an active agent for treating onychomycosis.

2. The method of claim 1, wherein determining an insertion point comprises determining the point of greatest curvature of the nail plate in a region defined by a longitudinal midline of the nail plate and a lateral nail fold.

3. The method of claim 1, wherein determining an insertion point comprises determining a point of onycholysis in a region defined by a longitudinal midline of the nail plate and a lateral nail fold.

4. The method of claim 1, further comprising after said determining, creating a subungual channel by inserting a cannula at the insertion point to form a subungual channel in the nail unit.

5. The method of claim 4, wherein the cannula is inserted to form a subungual channel that extends from the insertion point to approximately the visible proximal edge of fungal infection.

6. The method of claim 4, wherein said administering comprises administering by insertion at the insertion point a needle into the subungual channel.

7. The method of claim 6, wherein said administering comprises administering the composition in the subungual channel such that at least a portion of the composition extends beyond the visible proximal edge of fungal infection.

8. The method of claim 1, wherein determining comprises determining an insertion point for insertion of an instrument selected from a blunt end cannula and a needle.

9. The method of claim 8, wherein the instrument is a cannula, and the method further comprises inserting the cannula at the insertion point to approximately the visible proximal edge of fungal infection to create a subungual channel.

10. The method of claim 9, wherein administering comprises inserting a needle into the subungual channel, wherein the composition with an active agent is placed in a tip region of the needle.

11. The method of claim 10, wherein said administering comprises administering the composition in the subungual channel such that at least a portion of the composition extends beyond the visible proximal edge of fungal infection.

12. The method of claim 4, wherein the subungual channel extends distally from a distal edge of the nail plate to a proximal edge of fungal infection.

13. The method of claim 4, wherein creating a subungual channel comprises debriding subungual debris.

14. The method of claim 4, wherein creating further comprises depositing an anesthetic in the subungual channel.

15. The method of claim 1, wherein the composition is a solid composition, a semi-solid composition or a solution.

16. The method of claim 15, wherein the composition is a solid or a semi-solid composition comprised of a biodegradable polymer.

17. The method of claim 16, wherein the biodegradable polymer is polyethylene glycol.

18. The method of claim 1, wherein the active agent is an antifungal agent.

19. The method of claim 18, wherein the antifungal agent is terbinafine hydrochloride.

20. The method of claim 19, wherein the composition comprises between about 65-80 weight percent anti-fungal agent.

* * * * *